United States Patent [19]

Sinn

[11] Patent Number: 5,301,801
[45] Date of Patent: Apr. 12, 1994

[54] RETAINER PACKAGE FOR RESILIENT SURGICAL SUTURES

[75] Inventor: Hans-Jurgen F. Sinn, Fairfield, Conn.

[73] Assignee: United States Surgical Corporation, Norwalk, Conn.

[21] Appl. No.: 870,292

[22] Filed: Apr. 17, 1992

[51] Int. Cl.⁵ .............................................. A61B 17/06
[52] U.S. Cl. .............................. 206/63.300; 206/380; 206/495
[58] Field of Search ................. 206/63.3, 227, 380, 206/382, 485, 492, 495

[56] References Cited

U.S. PATENT DOCUMENTS

| | | |
|---|---|---|
| 2,617,523 | 11/1952 | Zoller . |
| 2,639,081 | 5/1953 | Metzger ............... 206/553 |
| 2,692,676 | 10/1954 | Grover ................ 206/63.3 |
| 3,062,372 | 11/1962 | Egler et al. . |
| 3,167,895 | 2/1965 | Egler et al. . |
| 3,280,971 | 10/1966 | Regan, Jr. . |
| 3,444,994 | 5/1969 | Kaepernik et al. . |
| 3,490,192 | 1/1970 | Regan, Jr. . |
| 3,627,120 | 12/1971 | Bordeau . |
| 3,876,068 | 4/1975 | Sonnino . |
| 3,939,969 | 2/1976 | Miller et al. . |
| 3,959,947 | 6/1976 | Sonnino . |
| 4,034,850 | 7/1977 | Mandel et al. ........ 206/63.3 |
| 4,121,711 | 10/1978 | Bolanowski .......... 206/63.3 |
| 4,142,628 | 3/1979 | Marocco et al. . |
| 4,168,000 | 9/1979 | MacRitchie . |
| 4,284,194 | 8/1981 | Flatau . |
| 4,369,880 | 1/1983 | Giggey et al. ........ 206/63.3 |
| 4,424,899 | 1/1984 | Thyen et al. . |
| 4,708,241 | 11/1987 | Black . |
| 4,813,537 | 3/1989 | Okuhara et al. ...... 206/380 |
| 4,887,710 | 12/1989 | Roshdy et al. ....... 206/63.3 |
| 4,946,043 | 8/1990 | Roshdy et al. . |
| 4,961,498 | 10/1990 | Kalinski et al. . |
| 4,967,902 | 11/1990 | Sobel et al. . |
| 5,101,968 | 4/1992 | Henderson et al. . |
| 5,174,087 | 12/1992 | Bruno ................ 206/63.3 |

*Primary Examiner*—David T. Fidei

[57] ABSTRACT

A retainer package is provided for receiving, and maintaining for ready removal, at least one resilient surgical suture in a coiled configuration. The package includes a plurality of interconnected panels which may be folded upon one another to form a means for housing the resilient sutures. The package is formed with a loading port defining a radially unobstructed passageway for receiving the resilient sutures coils. Structure may be associated with the package for securely maintaining surgical needles for ready removal.

15 Claims, 6 Drawing Sheets

RETAINER PACKAGE FOR RESILIENT SURGICAL SUTURES

BACKGROUND OF THE INVENTION

1. Field of the Invention

The invention relates to a new and useful suture retainer package and more particularly to a package for retaining at least one resilient surgical suture in a manner for ready removal.

2. Description of the Related Art

Many monofilament surgical sutures possess certain mechanical characteristics such as stiffness and a tendency to be wire-like and resilient. In the past, such sutures have been retained in packages manufactured in such a manner so as to enable the formation of upstanding projections within the package body around which the sutures could be wound in a peripheral storage channel. Examples of this type of package include: U.S. Pat. No. 4,424,898; U.S. Pat. No. 4,961,498; and U.S. Pat. No. 4,967,902. Retainers wherein a suture may be automatically fed through a notch provided in a partially assembled package, are described in U.S. Pat. No. 4,142,628.

These prior art suture retainer packages have not taken advantage of the resiliency of certain suture materials to aid in the loading of the package. Instead, prior art retainers have employed winding projections which may cause sutures to take an undesirable set when loaded into the package body.

It has been found that when a resilient monofilament surgical suture such as, for example, catgut or a similar material, is inserted into a package in a coil configuration the resilient suture will tend to uncoil within the package and expand radially outward so as to conform generally to the shape of the package. In accordance with this principle, it is desired to provide a suture retainer package with an internal cavity or retaining area which does not necessitate the formation of upstanding projections around which sutures must be wound to be loaded into the package. Such a suture retainer package permits a resilient surgical suture to be essentially self-loaded into an unrestricted retaining area.

Stated differently, it is an object of the subject invention to provide a suture retainer package into which a resilient suture coil may be loaded and thereafter caused to uncoil and expand radially outward within the package so as to be retained therein for ready removal.

It is another object of the subject invention to provide a suture retainer package which can be manufactured relatively inexpensively.

It is still another object of the subject invention to provide a suture retainer package for retaining a plurality of resilient surgical sutures.

It is yet another object of the subject invention to provide a suture retainer package which enables a plurality of resilient suture coils each having a needle affixed to one end to be loaded into the package in such a manner to enable ready removal.

It is yet a further object of the subject invention to provide a package for retaining a plurality of resilient surgical suture coils without taking an undesirable set.

It is still a further object of the subject invention to provide a new and useful needle park member which may be employed in the suture retainer package described herein.

SUMMARY OF THE INVENTION

The suture retainer package of the subject invention is provided for receiving and maintaining for ready removal, at least one resilient surgical suture arranged in a coiled configuration. The suture retainer package comprises a first panel having opposed top and bottom edges and opposed first and second lateral edges. A second panel is foldably connected to the first lateral edge of the first panel and has a primary aperture formed therein which is spaced from the periphery thereof in foldable alignment with the primary aperture. A third panel is foldably connected to the top edge of the first panel, and a fourth panel is foldably connected to the second lateral edge of the first panel. The fourth panel has a secondary aperture formed therein which is spaced from the periphery thereof. A fifth panel is foldably connected to the bottom edge of the first panel and includes a semi-circular notch portion which forms a section of a loading port. Means for locking the retainer package are provided and include a locking tab formed along an edge of the second panel for engagement in a locking slot formed along an edge of the fourth panel.

To construct the suture retainer package of the subject invention, the fourth panel is folded upon the first panel. Thereafter, the third and fifth panels are folded upon the fourth panel and the second panel is folded upon the third and fifth panels such that the primary and secondary apertures are in alignment. Once aligned, the superimposed apertures form a loading port which defines a radially unobstructed passageway into which at least one resilient surgical suture in a coil configuration may be loaded.

The retainer package of the subject invention may further include needle park means maintained in the suture retainer package. The needle park means would comprise a planar member having at least one central score line extending along the longitudinal axis thereof and serving to divide the planar member into first and second portions. The planar member may further have first and second lateral score lines, each of which would be spaced from, and parallel to the central score line. To form the needle park, the member may be folded along the central score line, and then along the first and second lateral score lines, to bring the first and second portions into opposition with a pair of opposed wing portions extending outwardly from the edges. At least one slit or opening extend across the central score line for releasably securing a surgical needle. Preferably, at least one slit extends generally perpendicular to the central score line and has a cross-slit or aperture defined therein proximate each end thereof for permitting lateral relaxation of the material defining the central score line during needle engagement. Means may also be provided for securely maintaining the needle park in a mounting slot formed in the retainer package.

Further features of the invention will become more readily apparent from the following detailed description of the invention taken in conjunction with the accompanying drawings.

BRIEF DESCRIPTION OF THE DRAWINGS

Preferred embodiments of the invention will be described hereinbelow with reference to the drawings wherein.

DETAILED DESCRIPTION OF THE PREFERRED EMBODIMENT

Figure 1:
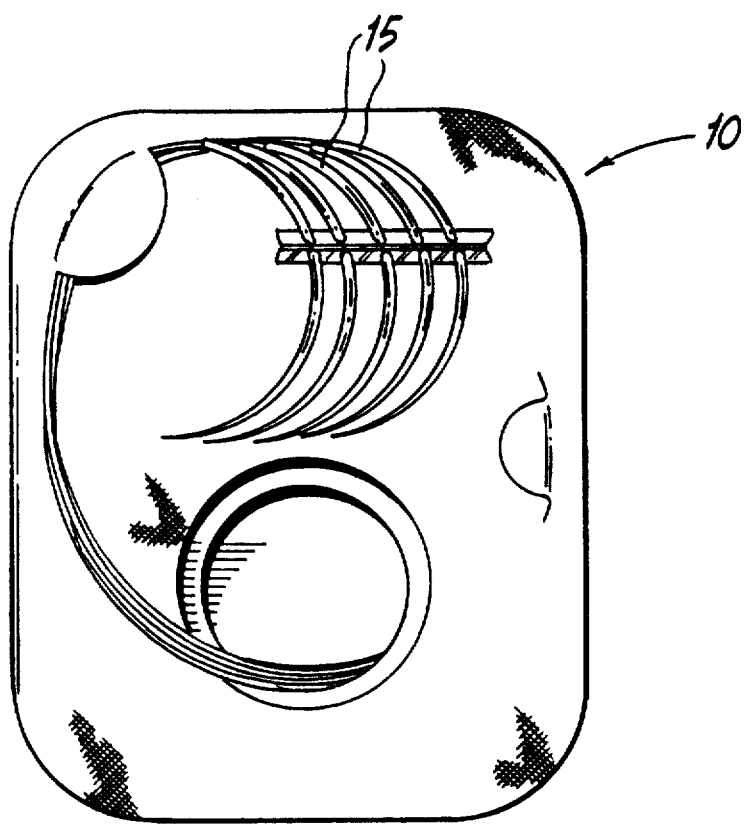
FIG. 1 is a perspective view of a suture retainer package in accordance with the preferred embodiment of the subject invention.
Figure 2:
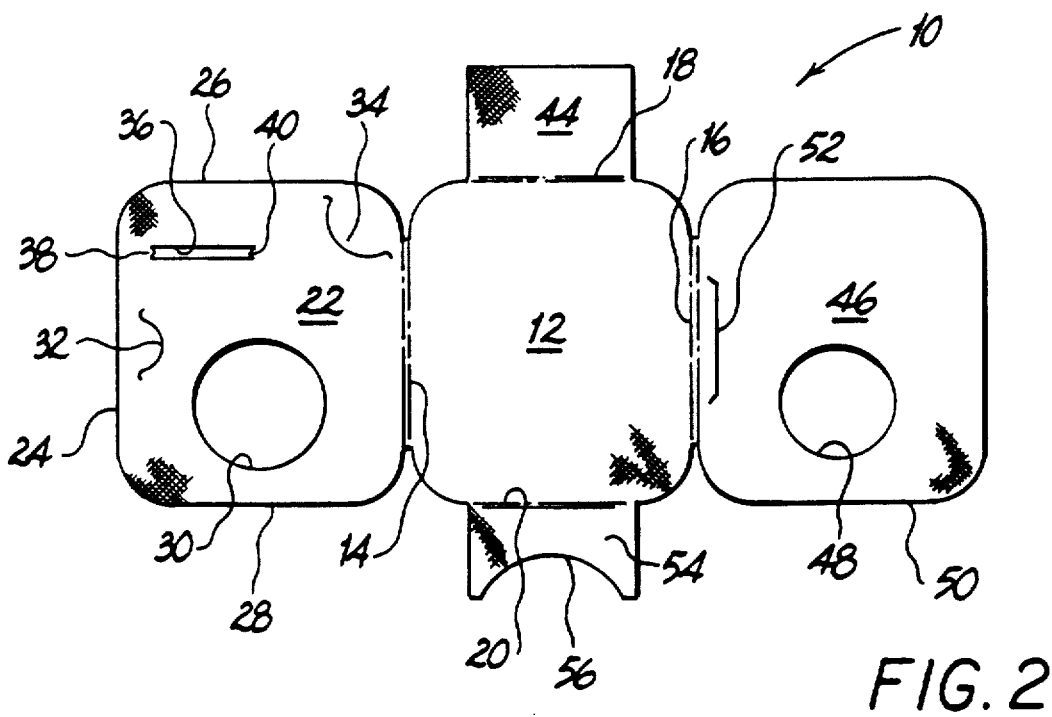
FIG. 2 is a top plan view of the package blank which forms the suture retainer of FIG. 1.

The suture retainer package of the subject invention is illustrated in FIG. 1 and is designated generally by reference numeral 10. Retainer package 10 is preferably made of a spun bonded polyolefin material, such as Tyvek ® (available from DuPont). Package 10 is provided for retaining, for ready removal, a plurality of armed surgical sutures 15. Referring to FIG. 2, package 10 comprises a first panel 12 having opposed lateral edges 14 and 16 and opposed top and bottom edges 18 and 20. A second panel 22 is foldably connected to the first panel 12 along lateral edge 14, and includes a side edge 24 and upper and lower edges 26 and 28. A primary aperture 30, which forms a portion of a loading port, is provided in the second panel 22 and is spaced from the lower edge 28 thereof. A locking tab 32 is formed in the second panel 22 adjacent the side edge 24 thereof, and a suture retaining tab 34 is provided adjacent the upper edge 26 thereof. An elongated mounting slot 36 is formed adjacent the upper edge 26 of the second panel 22 and includes a pair of opposed protuberances 38 and 40 which engage a needle park member 42 which may be mounted in the elongated mounting slot 36. Needle park member 42 will be discussed in greater detail hereinbelow.

A third panel 44 is foldably connected to the upper edge 18 of the first panel 12, and a fourth panel 46 is foldably connected to the first panel 12, along the lateral edge 16 thereof. A secondary aperture 48, which forms a portion of a loading port, is provided in the fourth panel 46 spaced from the bottom edge 50 thereof. A locking slit 52 is provided on the fourth panel 46 adjacent the lateral edge 16 of the first panel 12 and is dimensioned and positioned to lockingly receive the locking tab 32 of the second panel 22 when the suture retainer package 10 has been closed. A fifth panel 54 is foldably connected to the first panel 12 along the bottom edge 20 thereof, and includes a semi-circular notch portion 56 which corresponds to a portion of a loading port.

Figure 3:
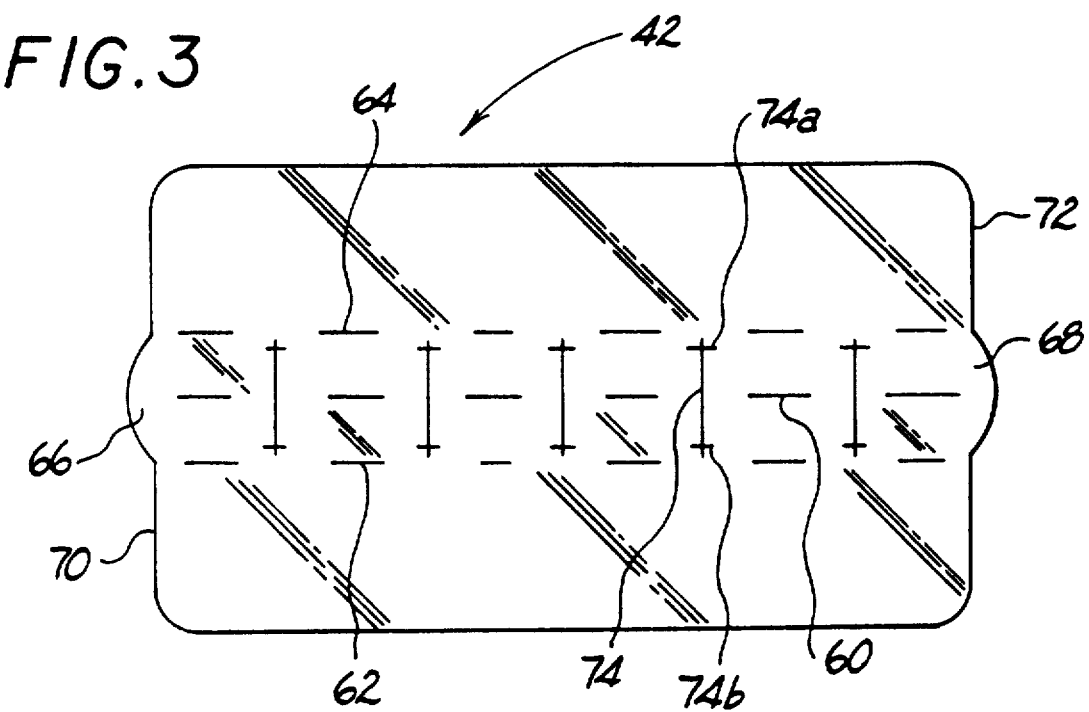
FIG. 3 is a top plan view of a needle park member which forms a portion of the retainer package of FIG. 1.

Referring to FIG. 3, the needle park member 42 is generally rectangular in configuration, and comprises a substantially planar piece of rigid material such as, for example 0.005 lb. Monadnock paper. Other materials of construction can be used such as plastics, cardboards or linerboards. Needle park member 42 has a central score line 60 which extends along the longitudinal axis thereof. The planar member can be folded along the central score line 60 to define opposed first and second structural portions which may be aligned to form a resilient member adapted for engagement in a mounting slot formed in a retainer package. Preferably, however, first and second lateral score lines 62 and 64 are defined on the needle park member 42, and are each equally spaced from, and parallel to the central score line 60. Arcurate flanges 66 and 68 extend from the side edges 70 and 72, respectively, for cooperating with the opposed protuberances 38 and 40 of mounting slot 36.

Figure 3A:
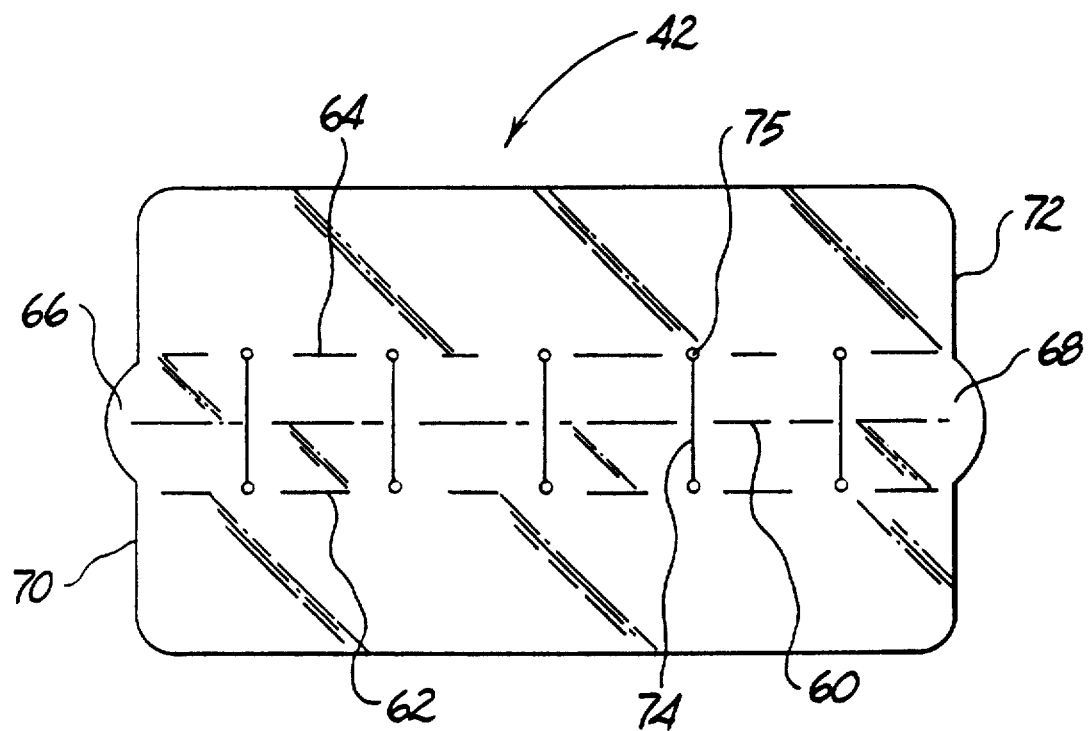
FIG. 3A, is a top plan view of an alternate needle park member in accordance with the subject invention.

A plurality of spaced apart needle mounting slits 74 are provided in the region between the opposed lateral score lines 62 and 64, through which surgical needles may be extended and retained for ready removal. Mounting slits 74 extend substantially perpendicular to the central score line 60 and are formed with orthogonal cross-slits 74a and 74b, disposed proximate each end thereof, for permitting relaxation of the material defining the mounting slits 74 during needle engagement. Alternatively, as best seen in FIG. 3A, the relaxation mechanism may comprise a circular aperture 75 formed at the ends of each mounting slit 74.

Figure 4:
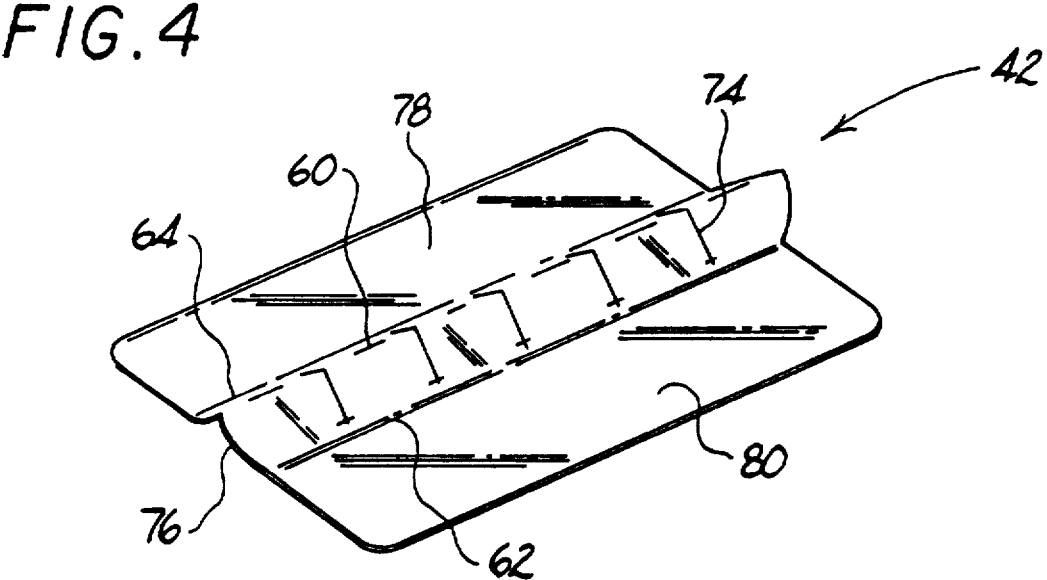
FIG. 4 is a perspective view of the folded needle park member of FIG. 3.
Figure 4A:
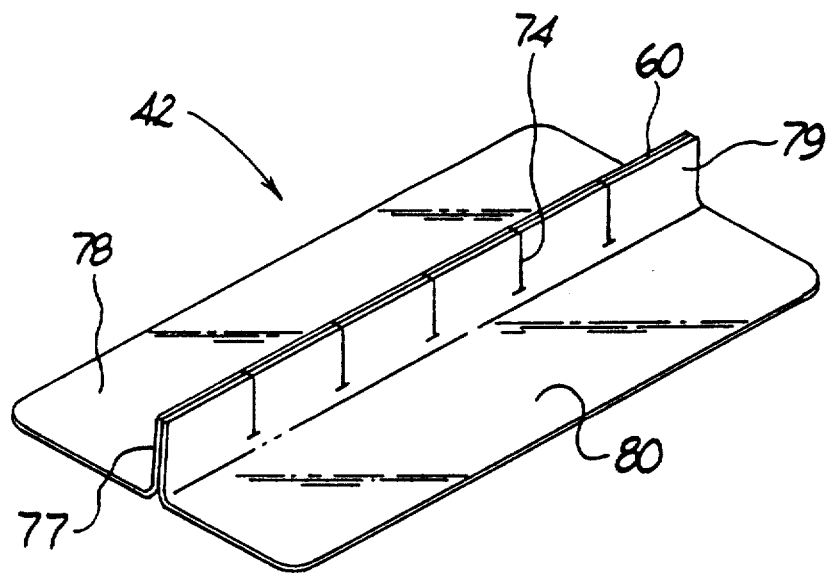
FIG. 4A, is a perspective view of the folded needle park member of FIG. 3A.

Referring to FIG. 4, the needle park 42 is formed by bending the generally rectangular member along the central score line 60 and thereafter, upon the lateral score lines 62 and 64, in such a manner so as to define a structure having a substantially inverted V-shaped channel portion 76, and opposed wing portions 78 and 80. Similarly, the needle park 42 may have a pair of centrally disposed score lines which would define a generally inverted U-shaped channel portion when the needle park 42 is formed. Alternatively, as best seen in FIG. 4A, opposed structural portions of the needle park member 42 may be brought into close opposed alignment to form substantially parallel side walls 77 and 79 with a plurality of transverse needle retaining slits 74 formed therein.

The needle park member 42 is mounted to the second panel 22 of retainer package 10 by extending the inverted V-shaped channel portion 76 into the mounting slot 36 so that the protuberances 38 and 40 extend into the area bounded by the inverted V-shaped channel portion 76. The arcuate flanges 66 and 68 serve to maintain the needle park 42 within the mounting slot 36. The engagement of needle park member 42 in mounting slot 36 is best seen in FIG. 1.

Needle park member 42 also may be mounted to the second panel 22 of retainer package 10 by applying an adhesive to the upper surface face of each of the wing portions 78 and 80 and thereafter, extending the V-shaped channel portion 76 through the mounting slot 36 so that the upper surface of each wing member is in face-to-face contact with panel 22. Alternatively, adhesive may be applied to the lower surface face of each of the wing portions 78 and 80 and thereafter, the needle park 42 can be affixed to panel 22 directly, after it is finally assembled.

Figure 5:
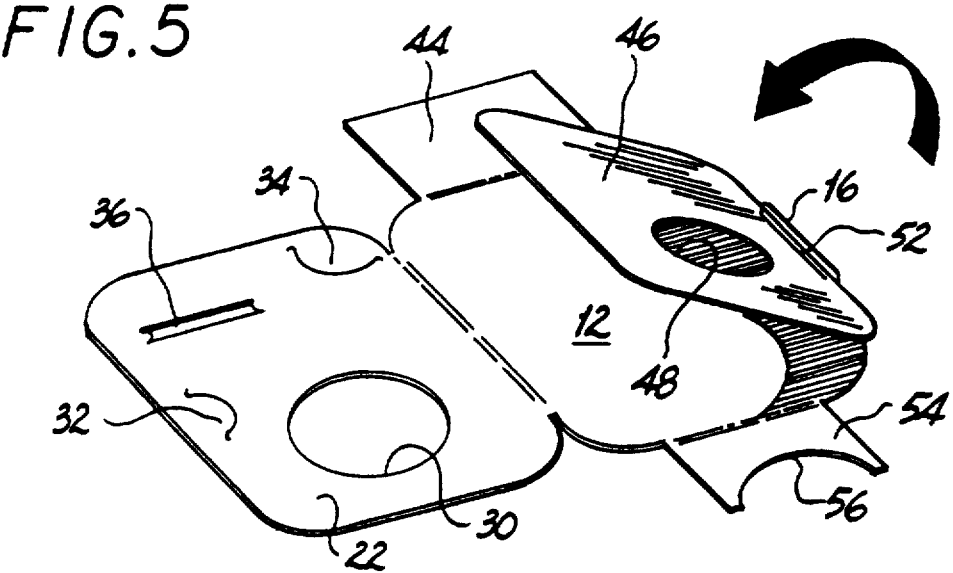
FIGS. 5-7 illustrate perspective views of the suture retainer package of FIG. 1, showing a sequence of steps for constructing the package from the blank of FIG. 2.
Figure 6:
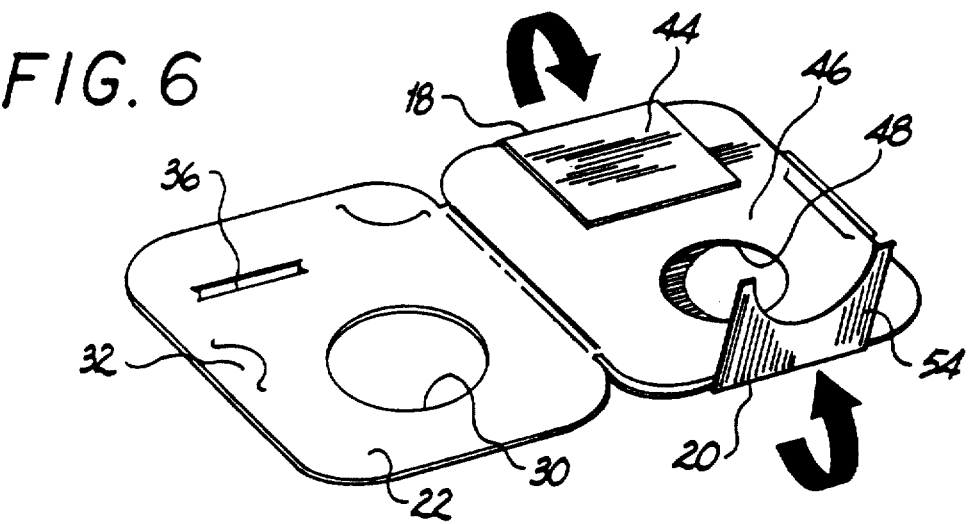
Figure 7:
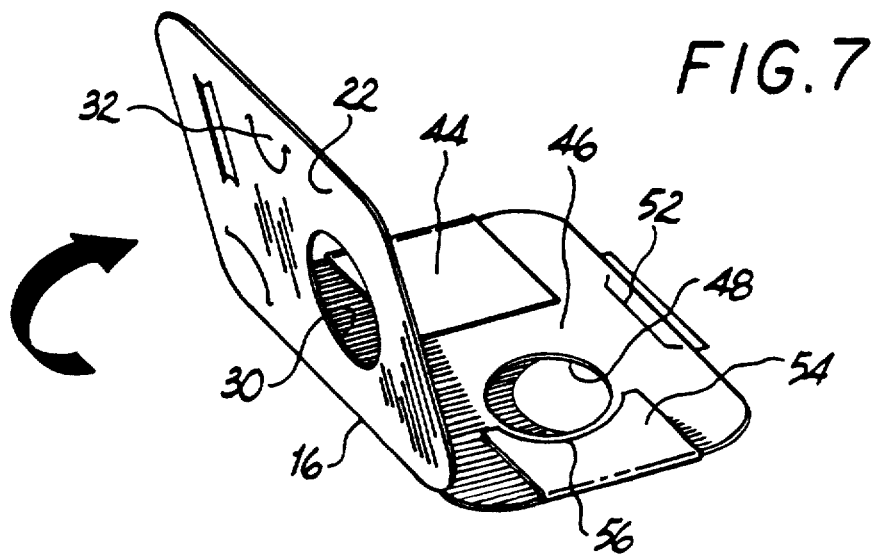

The needle park member 42 can be emplaced either before or after final assembly of the retainer package 10. Referring to FIGS. 5-7, initially, the fourth panel 46 of retainer package 10 is folded upon the first panel 12 along the lateral edge 16 thereof. Thereafter, the third panel 44 and the fifth panel 54 are folded upon the fourth panel 46, along top and bottom edges 18 and 20 thereof, respectively. At this time, the semi-circular notch portion 56 of panel 54 is superimposed on the secondary aperture 48 of the fourth panel 46. Then, the second panel 22 of retainer package 10 is folded upon the third panel 14 and the fifth panel 54, along the lateral edge 14 thereof. The primary aperture 30 superimposes on the secondary aperture 48 and notch portion 56, so as to define a radially unobstructed passageway into which resilient surgical sutures can be loaded in a coil configuration. Once the retainer package 10 has been formed, the locking tab 32 on the second panel 22 can be lockingly engaged in the locking slit 52 of the fourth panel 46, thereby securing the retainer package 10 in a loadable condition.

Figure 8:
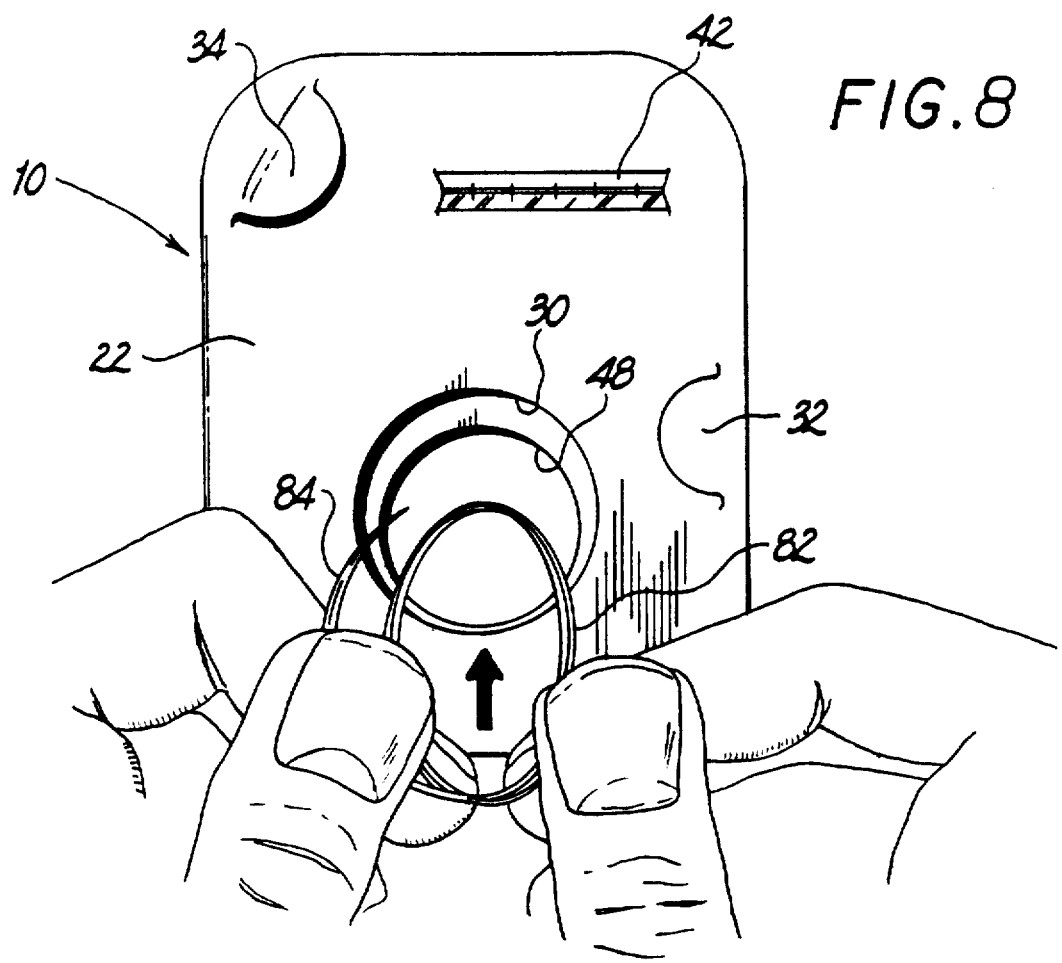
FIGS. 8-11 illustrate a sequence of steps for loading a resilient suture in a coiled configuration into the retainer package of FIG. 1.
Figure 9:
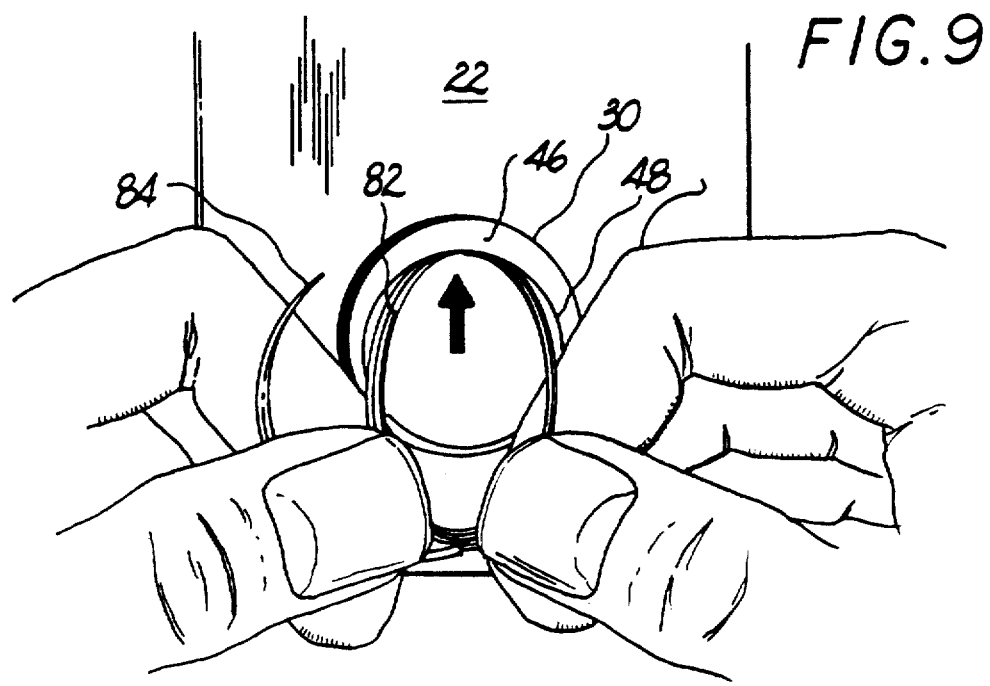
Figure 10:
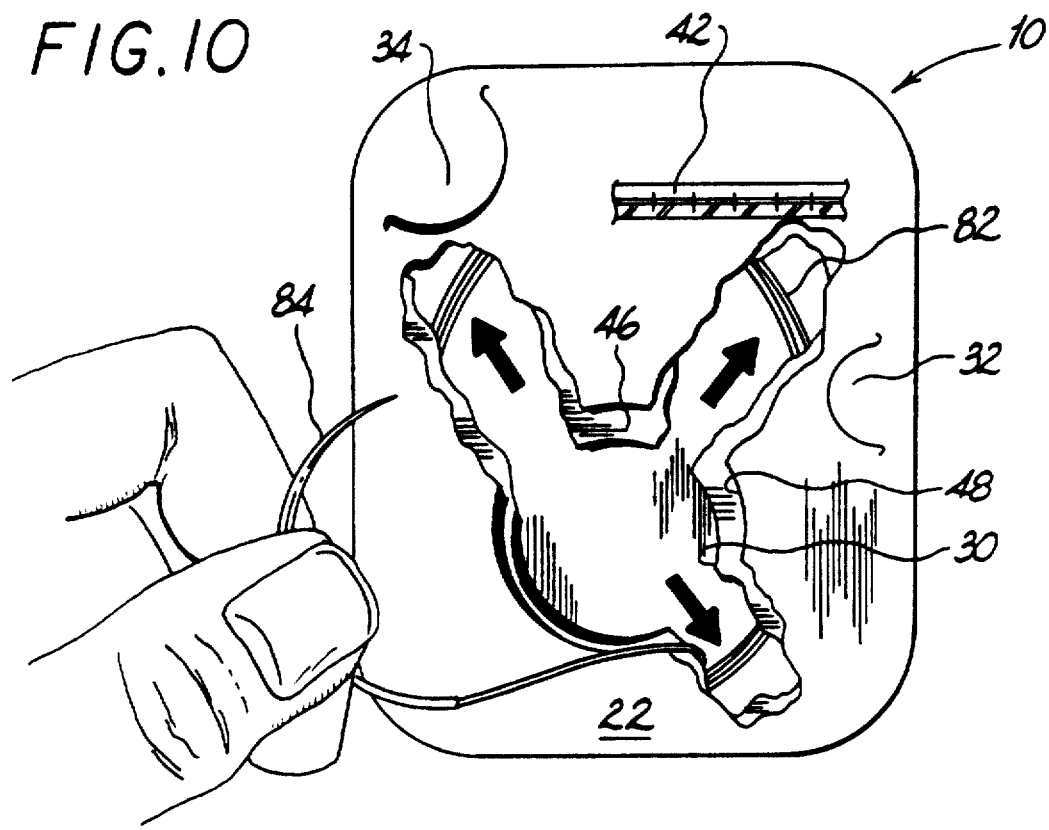
Figure 11:
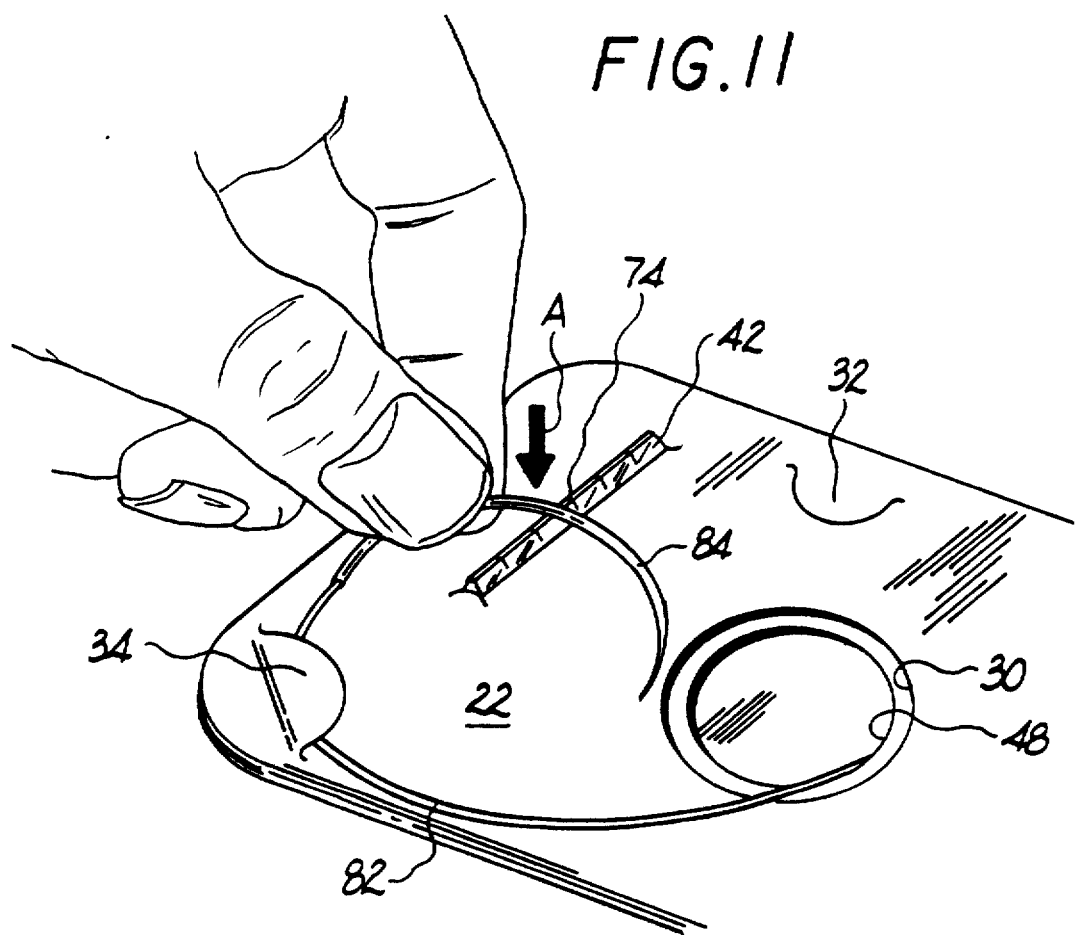

Referring to FIGS. 8-11, to load the suture retainer package 10 of the subject invention, a resilient surgical suture 82, preferably arranged in a coiled configuration with a surgical needle 84 affixed at one end, is directed toward the loading port defined by apertures 30 and 48, as illustrated by the indicator arrow in FIG. 8. Subsequently, the surgical suture coil 82 is inserted into the loading port 30,48 as shown by indicator arrow in FIG. 9. Thereupon, while grasping the surgical needle 84, the resilient surgical coil 82 is permitted to uncoil and expand radially outward within the retainer package 10, as illustrated by the indicator arrows in FIG. 10, so as to be maintained securely within the retainer package 10 for ready removal. The surgical needle 84 may then be directed towards the needle park 42 in the direction of indicator arrow "A" and inserted into mounting slit 74 so as to be securely maintained for ready removal. More particularly, once inserted, the secured portion of surgical needle 84 frictionally engages a portion of the material which defines mounting slit 74.

Although the subject invention has been described with respect to a preferred embodiment, it is apparent that changes may be made to the invention without departing from the spirit and scope thereof as defined by the appended claims.

What is claimed is:

1. A retainer package configured to be loaded in a folded condition and adapted for receiving at least one resilient surgical suture comprising:
   a first panel having opposed top and bottom edges and opposed first and second lateral edges;
   a second panel foldably connected to said first lateral edge of said first panel and having a primary aperture formed therein being spaced from a periphery thereof to permit loading of said at least one resilient suture into said package;
   a third panel foldably connected to said top edge of said first panel;
   a fourth panel foldably connected to said second lateral edge of said first panel and having a secondary aperture formed therein being spaced from a periphery thereof to permit loading of said at least one resilient suture into said package;
   a fifth panel foldably connected to said bottom edge of said first panel; and
   means for maintaining said retainer package in said folded condition for loading, said means for maintaining said retainer package including a locking tab formed along an edge of said second panel for engagement in a locking slit formed along an edge of said fourth panel whereby said fourth panel is folded upon said first panel, said third and fifth panels are folded upon said fourth panel, and said second panel is folded upon said third and fifth panels such that said primary and secondary apertures are in alignment so as to form a loading port which defines an unobstructed passageway for receiving said at least one resilient suture.

2. A retainer package as recited in claim 1, wherein said means for maintaining said retainer package comprises adhesive material.

3. A retainer package as recited in claim 1, wherein means are provided in said second panel for restricting the movement of at least one resilient surgical suture.

4. A retainer package configured to be loaded in a folded condition and adapted for receiving at least one resilient surgical suture comprising:
   a first panel having opposed top and bottom edges and opposed first and second lateral edges;
   a second panel foldably connected to said first lateral edge of said first panel and having a primary aperture formed therein being spaced from a periphery thereof to permit loading of said at least one resilient suture into said package;
   a third panel foldably connected to said top edge of said first panel;
   a fourth panel foldably connected to said second lateral edge of said first panel and having a secondary aperture formed therein being spaced from a periphery thereof to permit loading of said at least one resilient suture into said package;
   a fifth panel foldably connected to said bottom edge of said first panel;
   tab means for restricting the movement of at least one surgical suture integrally formed on said second panel; and
   means for maintaining said retainer package in said folded condition for loading, whereby said fourth panel is folded upon said first panel, said third and fifth panels are folded upon said fourth panel, and said second panel is folded upon said third and fifth panels such that said primary and secondary apertures are in alignment so as to form a loading port which defines an unobstructed passageway for receiving said at least one resilient suture.

5. A retainer package as recited in claim 1, wherein needle park means is associated with said package for releasably maintaining at least one surgical needle.

6. A retainer package as recited in claim 5, wherein means is provided on said second panel for mounting said needle park means.

7. A retainer package configured to be loaded in a folded condition and adapted for receiving at least one resilient surgical suture comprising:
   a first panel having opposed top and bottom edges and opposed first and second lateral edges:
   a second panel foldably connected to said first lateral edge of said first panel and having a primary aperture formed therein being spaced from a periphery thereof to permit loading of said at least one resilient suture into said package;
   a third panel foldably connected to said top edge of said first panel;
   a fourth panel foldably connected to said second lateral edge of said first panel and having a secondary aperture formed therein being spaced from a periphery thereof to permit loading of said at least one resilient suture into said package;
   a fifth panel foldably connected to said bottom edge of said first panel said fifth panel including a notched portion for registering with said primary aperture and said secondary aperture when said package is in said folded condition; and
   means for maintaining said retainer package in said folded condition for loading, whereby said fourth panel is folded upon said first panel, said third and fifth panels are folded upon said fourth panel, and said second panel is folded upon said third and fifth panels such that said primary and secondary apertures are in alignment so as to form a loading port which defines an unobstructed passageway for receiving said at least one resilient suture.

8. A retainer package for receiving at least one resilient surgical suture which comprises:

a) a first panel having opposed top and bottom edges and opposed first and second lateral edges;

b) a second panel foldably connected to said first lateral edge of said first panel and having a primary aperture formed therein being spaced from a periphery thereof;

c) a third panel foldably connected to said top edge of said first panel;

d) a fourth panel foldably connected to said second lateral edge of said first panel and having a secondary aperture formed therein being spaced from a periphery thereof;

e) a fifth panel foldably connected to said bottom edge of said first panel;

f) means for maintaining said retainer package in a folded condition for loading in which said primary and secondary apertures are in alignment so as to form a loading port which defines a radially unobstructed passageway for receiving said at least one resilient suture coil;

g) a mounting slot formed in said second panel; and h) a needle park comprising a polygonal planar member including:

i) at least one central score line extending along a longitudinal axis of said planar member;

ii) first and second lateral score lines each spaced from and extending substantially parallel to said at least one central score line;

iii) means for maintaining said needle park in said mounting slot; and iv) means for releasably securing at least one surgical needle in said needle park, whereby said needle park is formed by bending said planar member along said at least one central score line and said lateral score lines in such a manner so as to define a channel portion and opposed wing portions.

9. A retainer package as recited in claim 4, wherein said means for maintaining said retainer package includes a locking tab formed along an edge of said second panel for engagement in a locking slit formed along an edge of said fourth panel.

10. A retainer package as recited in claim 4, wherein needle park means is associated with said package for releasably maintaining at least one surgical needle.

11. A retainer package as recited in claim 10, wherein means is provided on said second panel for mounting said needle park means.

12. A retainer package as recited in claim 7, wherein said means for maintaining said retainer package includes a locking tab formed along an edge of said second panel for engagement in a locking slit formed along an edge of said fourth panel.

13. A retainer package as recited in claim 7, wherein said means for maintaining said retainer package comprises adhesive material.

14. A retainer package as recited in claim 7, wherein needle park means is associated with said package for releasably maintaining at least one surgical needle.

15. A retainer package as recited in claim 13, wherein means is provided on said second panel for mounting said needle park means.

* * * * *